United States Patent [19]

Caton et al.

[11] 4,171,375

[45] Oct. 16, 1979

[54] CYCLOPENTANE DERIVATIVES AND THEIR PHARMACEUTICAL COMPOSITIONS

[75] Inventors: Michael P. L. Caton, Upminster; Trevor Parker, Romford, both of England; Gordon L. Watkins, Santa Monica, Calif.

[73] Assignee: May & Baker Limited, Essex, England

[21] Appl. No.: 758,797

[22] Filed: Jan. 12, 1977

[30] Foreign Application Priority Data

Jan. 14, 1976 [GB] United Kingdom ................ 1384/76

[51] Int. Cl.² .............. A61K 31/19; A61K 31/20; A61K 31/215; A61K 31/22; C07C 61/38; C07C 69/145; C07C 69/74; C07C 69/78
[52] U.S. Cl. ........................ 424/305; 260/405; 260/410.9 R; 260/413; 260/501.1; 424/263; 424/308; 424/311; 424/316; 424/319; 424/318; 560/106; 560/121; 560/231; 560/240; 562/503; 546/348; 546/269
[58] Field of Search .............. 260/514 K, 413, 295 S, 260/410.9 R, 405, 501.1; 560/121, 231, 106; 424/305, 308, 311, 316, 317, 318, 263; 562/503

[56] References Cited

U.S. PATENT DOCUMENTS

| | | | |
|---|---|---|---|
| 3,880,883 | 4/1975 | Caton et al. | 560/231 |
| 3,923,872 | 12/1975 | Caton et al. | 560/231 |
| 3,950,406 | 4/1976 | Brawner et al. | 560/231 |
| 3,968,141 | 7/1976 | Sih et al. | 560/121 |
| 3,969,391 | 7/1976 | Poppo et al. | 560/121 |

*Primary Examiner*—Vivian Garner
*Attorney, Agent, or Firm*—Stevens, Davis, Miller & Mosher

[57] ABSTRACT

Cyclopentane derivatives of the formula:

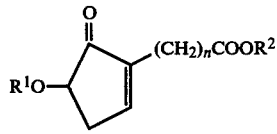

wherein $R^1$ represents hydrogen or a carboxylic acyl group, $R^2$ represents hydrogen or alkyl of 1 through 12 carbon atoms, and n represents an integer from 4 through 8, are new compounds possessing pharmacological properties, more particularly the production of hypertension and inhibition of gastric acid secretion. They are also useful in the preparation of 10-hydroxy-prostaglandins.

8 Claims, No Drawings

CYCLOPENTANE DERIVATIVES AND THEIR PHARMACEUTICAL COMPOSITIONS

This invention relates to novel cyclopentane derivatives, to a process for their preparation, and pharmaceutical compositions containing them.

According to the present invention, there are provided the new cyclopentane derivatives of the general formula:

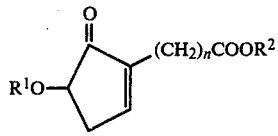

[wherein $R^1$ represents a hydrogen atom or a carboxylic acyl group, for example a straight- or branched-chain alkanoyl group containing from 1 to 5 carbon atoms or a benzoyl group, $R^2$ represents a hydrogen atom or a straight- or branched-chain alkyl group containing from 1 to 12 (for example from 1 to 4 or from 7 to 12) carbon atoms and n represents an integer from 4 to 8, preferably 6] and, when $R^2$ represents a hydrogen atom, salts thereof, for example salts of alkali metals (e.g. sodium or potassium), alkaline earth metals (e.g. calcium or magnesium), ammonia, or amines (e.g. ethylamine, triethylamine or pyridine).

As will be apparent to those skilled in the art, the structure shown in general formula I has at least one centre of chirality, that centre of chirality being at the ring carbon atom to which the group $R^1O-$ is attached. In addition to that centre of chirality, further centres of chirality may occur in acyl or alkyl groups represented by the symbols $R^1$ and $R^2$ respectively. The presence of centres of chirality, as is well known, leads to the existence of isomerism. Accordingly, all isomers of general formula I, and mixtures thereof, are within the scope of the present invention.

The compounds of formula I and, when $R^2$ represents a hydrogen atom, non-toxic salts thereof possess valuable pharmacological properties including, in particular, the production of hypertension and inhibition of gastric acid secretion. In laboratory screening tests compounds within formula I have been found to produce:

(a) a 10 mm Hg rise in the mean blood pressure of the urethane-anaesthetised, pempidine-treated normotensive rat at doses between 20 and 50 μg/kg animal body weight, administered intravenously; and (b) an inhibition of pentagastrin-induced gastric acid secretion in the rat of between 10 and 35% at a dose of 50 μg/kg animal body weight/minute when administered orally in solution in an aqueous sodium chloride solution for 60 minutes.

The compounds are accordingly of use in the treatment or prevention of low blood pressure or the inhibition of gastric acid secretion.

The compounds of formula I and, where applicable, salts thereof are also useful as intermediates in the preparation of 10-hydroxyprostaglandins and derivatives and analogues thereof. Prostaglandins have useful pharmacological properties, for example the production of hypotension, bronchodilatation, inhibition of gastric acid secretion, and stimulation of uterine contraction, and accordingly they are of utility as pharmaceuticals and as constituents in pharmaceutical compositions.

According to a further feature of the present invention, the compounds of formula I are prepared by the reaction of a compound of the general formula:

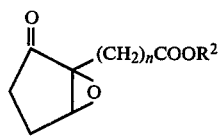

(wherein $R^2$ and n are as hereinbefore defined) with an inorganic acid or a carboxylic acid of the formula $R^{1'}-OH$ (wherein $R^{1'}$ represents a carboxylic acyl group), preferably as the reaction medium, and preferably at an elevated temperature, for example the reflux temperature of the reaction mixture.

When the acid reagent is an inorganic acid, the compound of formula I obtained is one wherein $R^1$ represents a hydrogen atom and $R^2$ and n are as hereinbefore defined. Preferably the reaction is carried out with a dilute inorganic acid, for example dilute sulphuric acid, preferably in the presence of an inert organic solvent, e.g. acetone or dioxan.

When the acid reagent is a carboxylic acid, the compound of formula I obtained is one wherein $R^1$ represents the acyl group corresponding to the carboxylic acyl group $R^{1'}$ of the acid used, and $R^2$ and n are as hereinbefore defined.

Compounds of formula II are prepared by the epoxidation of a compound of the general formula:

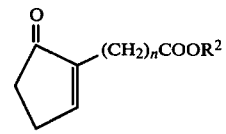

(wherein $R^2$ and n are as hereinbefore defined), preferably by reaction with hydrogen peroxide and an alkali metal hydroxide (e.g. sodium hydroxide) in an inert organic solvent, for example an alkanol containing from 1 to 4 carbon atoms (e.g. methanol) at a temperature near or below the ambient temperature, preferably at between 0° and 25° C.

Compounds of formula III wherein $R^2$ represents a hydrogen atom and n is as hereinbefore defined are prepared by the oxidation of a compound of the general formula:

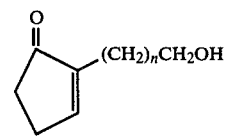

(wherein n is as hereinbefore defined), preferably by the action of chromium trioxide and aqueous sulphuric acid in the presence of an inert organic solvent, e.g. acetone, at a temperature near or below the ambient temperature.

Compounds of formula IV are prepared by the reaction of a compound of the general formula:

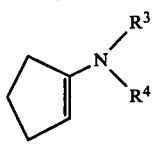

(wherein $R^3$ and $R^4$ each represents an alkyl group or together $R^3$ and $R^4$ represent a 4- or 5-membered hydrocarbon chain, which may be interrupted by one or two oxygen or nitrogen atoms—where such additional nitrogen atoms are of the form

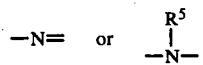

in which $R^5$ represents an alkyl group—the carbon atoms in the said hydrocarbon chain optionally each carrying 1 and 2 alkyl groups) with an aldehyde of the general formula:

$$R^6O(CH_2)_nCHO \qquad VI$$

wherein $R^6$ represents a hydrogen atom or a 2-tetrahydropyranyl group unsubstituted or substituted by, for example, at least one alkyl group and n is as hereinbefore defined. The reaction is carried out by heating the reactants in an inert organic solvent, for example an aromatic hydrocarbon (e.g. benzene) with continuous removal of water, preferably at between 60° and 120° C., followed by hydrolysis in aqueous acid conditions (e.g. with hydrochloric acid), preferably at ambient temperature, and then heating with an acid (e.g. concentrated hydrochloric acid), preferably at about 100° C., and preferably in an inert organic solvent such as an alcohol (e.g. butanol), to cause the double bond to migrate from the exocyclic to the endocyclic position.

According to a further feature of the present invention, compounds of formula I wherein $R^2$ represents an alkyl group of 1 to 12 carbon atoms and $R^1$ and n are as hereinbefore defined are prepared by the esterification of a corresponding carboxylic acid of formula I wherein $R^2$ represents a hydrogen atom by the application or adaptation of known methods for the esterification of carboxylic acids.

Thus, the esterification can be carried out by reaction of the carboxylic acid with (i) an alcohol of the general formula:

$$R^7OH \qquad VII$$

(wherein $R^7$ represents a straight- or branched-chain alkyl group containing from 1 to 12 carbon atoms), an excess of which may be employed as solvent medium, in the presence of an inorganic acid, e.g. hydrochloric acid or sulphuric acid, preferably at a temperature between 50° and 160° C., and advantageously at the reflux temperature of the reaction mixture, or (ii) in the case where the desired ester is a compound of the formula I, wherein $R^2$ represents a group of the formula —$CHR^8R^9$ (wherein the symbols $R^8$ and $R^9$ are identical or different and each represents an alkyl group or, preferably, a hydrogen atom, the total number of carbon atoms in the group —$CHR^8R^9$ being at most 12), by reaction with a diazoalkane of the general formula:

$$R^8R^9C{=}N_2 \qquad VIII$$

(wherein $R^8$ and $R^9$ are as hereinbefore defined) in an inert organic solvent, preferably a dialkyl ether (e.g. diethyl ether), preferably at ambient temperature.

Alternatively, a silver salt of such a carboxylic acid of formula I can be reacted with an alkyl halide of the general formula:

$$R^7Z^1 \qquad IX$$

(wherein $Z^1$ represents a halogen atom and $R^7$ is as hereinbefore defined), optionally in the presence of an inert organic solvent, for example an aromatic hydrocarbon (e.g. benzene), at elevated temperature, for example at between 40° and 110° C., and advantageously at the reflux temperature of the reaction mixture.

Compounds of formula III wherein $R^2$ represents an alkyl group of 1 to 12 carbon atoms and n is as hereinbefore defined may be prepared by the esterification of a corresponding carboxylic acid of formula III wherein $R^2$ represents a hydrogen atom, by the application or adaptation of the methods hereinbefore described for the esterification of carboxylic acids of formula I.

According to another feature of the invention, compounds of formula I wherein $R^1$ represents a hydrogen atom are prepared by the hydrolysis by known methods of corresponding compounds of that formula wherein $R^1$ represents a carboxylic acyl group, for example by the action of an alkali metal carbonate, e.g. sodium carbonate, in an aqueous alkanolic medium, e.g. aqueous methanol.

As a further feature of the present invention, salts of the carboxylic acids of formula I wherein $R^2$ represents a hydrogen atom ($R^1$ and n being as hereinbefore defined) are prepared by the application or adaptation of known methods for the preparation of salts of carboxylic acids, for example by reaction of stoichiometric quantities of an acid of formula I (wherein $R^2$ represents a hydrogen atom) and the appropriate base, e.g. an alkali or alkaline earth metal hydroxide or carbonate, ammonium hydroxide, ammonia or an amine, in a suitable solvent, which is preferably water in the case of the preparation of alkali metal salts and water or isopropanol in the case of amine salts. The salts may be isolated by lyophilisation of the solution or, if sufficiently insoluble in the reaction medium, by filtration, if necessary after removal of part of the solvent.

As well as being useful in themselves and as intermediates for the preparation of prostaglandins and derivatives and analogous thereof, salts of acids of formula I, wherein $R^2$ represents a hydrogen atom, can be used for the purposes of purification of the parent acids of formula I, for example by exploitation of the solubility differences between the salts and the parent acids in water and in organic solvents, by techniques well known to those skilled in the art. The parent acids of formula I can be regenerated from their salts by known methods, for example by treatment with an inorganic acid e.g. dilute hydrochloric acid.

It is to be understood that where in this specification reference is made to compounds of formula I, it is intended to refer also, where the context so permits, to the said salts of the compounds of formula I wherein $R^2$ represents a hydrogen atom.

As will be readily appreciated by those skilled in the art, the enantiomeric forms of the compounds of the invention arising from the aforementioned centre(s) of chirality may be separated by the application or adaptation of known methods, for example enantiomeric forms of acidic compounds of formula I wherein $R^2$ represents a hydrogen atom may be separated by formation of salts with an optically active base, followed by separation of the obtained pair of diastereoisomers by, for example, fractional crystallisation from a suitable solvent system, followed by separate regeneration of the enantiomeric acids of formula I.

The 10-hydroxyprostaglandins and derivatives and analogues thereof which may be prepared from the compounds of formula I include those compounds of the general formula:

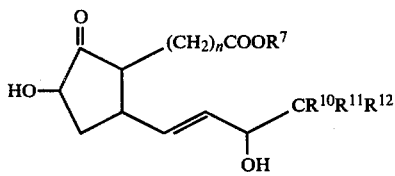

wherein $R^7$ represents a straight- or branched-chain alkyl group containing from 1 to 12 (preferably from 1 to 4 or from 7 to 12) carbon atoms, $R^{10}$ and $R^{11}$ have the same or different significances and each represents a hydrogen atom or a straight- or branched-chain alkyl group containing from 1 to 4 carbon atoms, $R^{12}$ represents a hydrogen atom or, preferably, a straight- or branched-chain alkyl group containing from 1 to 10 (preferably 3, 6 or, more particularly, 4) carbon atoms and n represents an integer from 4 to 8, preferably 6.

In the compounds of formula X the vinylene group in the side-chain $-CH=CH-CH(OH)-CR^{10}R^{11}R^{12}$ is in the trans-configuration.

As will be apparent to those skilled in the art, the structure shown in general formula X has at least four centres of chirality, three of these centres of chirality being at the ring carbon atoms to which the hydroxy group and the side-chains $-(CH_2)_nCOOR^7$ and $-CH=CH-CH(OH)-CR^{10}R^{11}R^{12}$ are attached, and the fourth centre of chirality is at the carbon atom in the hydroxymethylene group in the side-chain $-CH=CH-CH(OH)-CR^{10}R^{11}R^{12}$. Still further centres of chirality may occur in the group $-CR^{10}R^{11}R^{12}$ or in alkyl groups represented by the symbols $R^7$, $R^{10}$, $R^{11}$ and $R^{12}$. The presence of centres of chirality, as is well known, leads to the existence of isomerism. However, the compounds of formula X all have a configuration such that the side-chains $-(CH_2)_nCOOR^7$ and $-CH=CH-CH(OH)-CR^{10}R^{11}R^{12}$ are trans with respect to each other.

The system of nomenclature described by Nelson, J. Med. Chem., 17(9), (1974), 911–918, is employed in the present specification in respect of compounds of formula X.

The compounds of formula X possess valuable pharmacological properties including, for example, the production of hypotension, bronchodilatation, inhibition of gastric acid secretion, and stimulation of uterine contraction, and central nervous system depressant activity.

In laboratory tests (±)-(10R and S, 15S)-11-deoxy-10-hydroxyprostaglandin $E_1$ methyl ester was 0.3 times as active as the natural product prostaglandin $E_1$ in stimulating uterine contraction in the rat, and its duration of activity was between 3 and 7 minutes when administered intravenously.

In the anaesthetised cat, (±)-(10R and S, 15S)-11-deoxy-10-hydroxyprostaglandin $E_1$ methyl ester was 0.2 times as active as prostaglandin $E_1$ in producing a 20 mm Hg fall in diastolic blood pressure when administered intravenously.

Compounds of formula X are prepared by the reaction of compounds of the general formula:

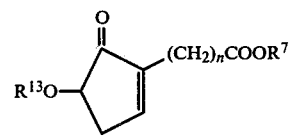

(wherein $R^7$ and n are as hereinbefore defined, and $R^{13}$ represents a suitable acid labile protecting group) with a solution of a compound of the general formula:

$$Li-CH=CH-CH(OR^{13})-CR^{10}R^{11}R^{12} \quad \text{XII}$$

(wherein $R^{10}$, $R^{11}$, $R^{12}$ and $R^{13}$ are as hereinbefore defined) in an ether, e.g diethyl ether or tetrahydrofuran, in the presence of a copper compound, preferably a cuprous copper compound soluble in the ether solvent, in anhydrous conditions, in an inert atmosphere (e.g. nitrogen or argon), and at a low temperature (preferably between $-10°$ and $-80°$ C., more particularly between $-15°$ and $-25°$ C.), to form products of the general formula:

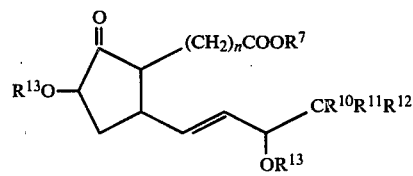

(wherein $R^7$, $R^{10}$, $R^{11}$, $R^{12}$, $R^{13}$ and n are as hereinbefore defined, the groups represented by the symbol $R^{13}$ being the same or different), followed by hydrolysis of the compounds of formula XIII in mild acidic conditions (for example in 60–80% v/v aqueous acetic acid in the presence of an inert organic solvent, e.g. diethyl ether or tetrahydrofuran, preferably at a temperature between 15° and 50° C.) to form compounds of formula X.

Suitable acid labile protecting groups represented by $R^{13}$ are those which are easily removed by acid hydrolysis and which do not cause side reactions, e.g. a 2-tetrahydropyranyl group unsubstituted or substituted by at least one straight- or branched-chain alkyl group containing from 1 to 4 carbon atoms, or a 2-tetrahydrofuranyl group, or a trialkylsilyl group of the general formula:

$$-SiR^{14}R^{15}R^{16} \quad \text{XIV}$$

(wherein $R^{14}$ and $R^{15}$, which may be the same or different, each represents a methyl or ethyl group and $R^{16}$ represents a straight- or branched-chain alkyl group containing from 1 to 4 carbon atoms), e.g. a trimethylsilyl, dimethylisopropylsilyl or tert-butyldimethylsilyl group, or a 1-alkoxyalkyl group of the general formula:

$$-CH(CH_2R^{17})OR^{18} \quad \text{XV}$$

(where $R^{17}$ represents a hydrogen atom or a straight- or branched-chain alkyl group containing from 1 to 4 carbon atoms and $R^{18}$ represents a straight- or branched-chain alkyl group containing from 1 to 4 carbon atoms) e.g. a 1-ethoxyethyl group.

Suitable copper compounds include complexes formed by an alkynyl copper, e.g. pentynyl copper, with a water-soluble tertiary phosphine, e.g. hexamethylphosphorus triamide, or, more particularly, complexes formed by a cuprous halide, e.g. cuprous iodide, with compounds of the general formulae:

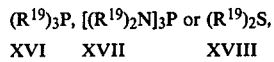

$(R^{19})_3P$, $[(R^{19})_2N]_3P$ or $(R^{19})_2S$,
XVI  XVII  XVIII or with ligands of the general formulae:

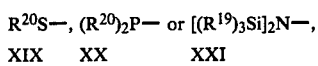

$R^{20}S-$, $(R^{20})_2P-$ or $[(R^{19})_3Si]_2N-$,
XIX  XX  XXI wherein $R^{19}$ represents a straight- or branched-chain alkyl group containing from 1 to 4 carbon atoms and $R^{20}$ represents an aryl, e.g. phenyl, group.

The compounds of formula XII and the copper compounds may be prepared by the application or adaptation of known methods, for example methods described by Sih et al, J.A.C.S., 97 (1975), 857–874 and by Corey et al, J.A.C.S. 94, (1972), 7210.

Compounds of formula XI may be prepared from compounds of the general formula:

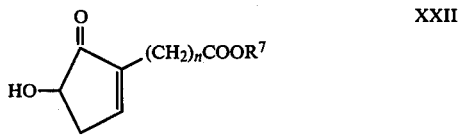

XXII (wherein $R^7$ and n are as hereinbefore defined), i.e. compounds within general formula I, by the application or adaptation of known methods.

For example, compounds of formula XI wherein $R^{13}$ represents a 2-tetrahydropyranyl group unsubstituted or substituted by at least one straight- or branched-chain alkyl group containing from 1 to 4 carbon atoms, or a 2-tetrahydrofuranyl group or a 1-alkoxyalkyl group of formula XV (wherein $R^{17}$ and $R^{18}$ are as hereinbefore defined) may be prepared by the reaction of compounds of formula XXII with 2,3-dihydropyran or the appropriate alkylated, 2,3-dihydropyran, or with 2,3-dihydrofuran or with a compound of the general formula:

$R^{17}CH=CHOR^{18}$  XXIII (wherein $R^{17}$ and $R^{18}$ are as hereinbefore defined), e.g. ethyl vinyl ether, in the presence of a catalytic quantity of an acid, for example an inorganic acid (e.g. concentrated hydrochloric acid) or a strong organic acid (e.g. p-toluenesulphonic acid). The reaction is preferably carried out in the presence of an inert organic solvent, for example a halogenated hydrocarbon, e.g. dichloromethane, at a temperature between 15° and 75° C., preferably between 20° and 40° C.

Compounds of formula XI wherein $R^{13}$ represents a trialkylsilyl group of formula XIV (wherein $R^{14}$, $R^{15}$ and $R^{16}$ are as hereinbefore defined) may be prepared by the reaction of compounds of formula XXII with a hexaalkyldisilazane of the general formula:

$R^{16}R^{15}R^{14}Si-NH-SiR^{14}R^{15}R^{16}$  XXIV (wherein $R^{14}$, $R^{15}$ and $R^{16}$ are as hereinbefore defined) in the presence of a trialkylchlorosilane of the formula $R^{16}R^{15}R^{14}SiCl$ ($R^{14}$, $R^{15}$ and $R^{16}$ being as hereinbefore defined) or hydrogen chloride gas, under anhydrous conditions, for example in dry tetrahydrofuran as solvent.

By the term "known methods" as used in the present specification is meant methods heretofore used or described in the literature.

The following Examples 1, 2 and 3 illustrate the preparation of the new compounds of formula I. Their use in the preparation of compounds of formula X is illustrated in the reference Example which follows them.

EXAMPLE 1

A solution of (±)-7-(1,2-epoxy-5-oxocyclopentyl)heptanoic acid (3.0 g) in glacial acetic acid (75 ml) was heated at reflux for 8 hours. The excess acetic acid was then removed in vacuo to give an oil which crystallised on standing. Recrystallisation from a mixture of water and ethanol gave (±)-7-(4-acetoxy-5-oxocyclopent-1-enyl)heptanoic acid (1.4 g), m.p. 62°–65° C.

Elemental analysis: found C, 62.9; H 7.8%; $C_{14}H_{20}O_5$ requires C, 62.7; H, 7.5%.

The nuclear magnetic resonance spectrum (N.M.R.) of a 10% solution of the (±)-7-(4-acetoxy-5-oxocyclopent-1-enyl)heptanoic acid in deuterochloroform displayed the following peaks:

multiplets at 2.45δ and 3.0δ (J=19 cycles/second) (ring methylene group).
triplet at 2.30δ (chain methylene group adjacent to carboxy group),
singlet at 2.1δ (acetoxy group),
multiplet at 2.0δ–2.5δ (chain methylene group adjacent to ring).

The (±)-7-(1,2-epoxy-5-oxocyclopentyl)heptanoic acid used in the above preparation was obtained as follows:

A stirred solution of 7-(5-oxocyclopent-1-enyl)heptanoic acid (16.5 g) in methanol (400 ml) was treated slowly with aqueous hydrogen peroxide solution (32 ml; 100 volume strength) and 4N sodium hydroxide solution (28 ml) at 5° to 10° C. and allowed to stand at room temperature for 18 hours. The solution was concentrated in vacuo (to a volume of about 100 ml) and water (100 ml) was then added to the residue. The mixture was washed with chloroform and the chloroform discarded. The aqueous solution was then acidified to pH 3 by means of glacial acetic acid. The mixture was extracted with chloroform and the chloroform extract was washed with water and dried over magnesium sulphate. The solvent was removed in vacuo to give (±)-7-(1,2-epoxy-5-oxocyclopentyl)heptanoic acid (16.0 g), pure enough for use in the preparation of (±)-7-(4-acetoxy-5-oxocyclopent-1-enyl)heptanoic acid without further purification.

The 7-(5-oxocyclopent-1-enyl)heptanoic acid used in the above preparation was obtained as follows:

8N Jones reagent [90 ml; prepared by dissolving chromium trioxide (24.0 g) in a small volume of water, treating carefully with concentrated sulphuric acid (20.7 ml) and diluting with water to 90 ml with cooling] was added to a stirred solution of 2-(7-hydroxyheptyl)-cyclopent-2-enone (39.2 g) in acetone (400 ml) at 10°–22° C. at a rate such that the deep red colouration caused by the addition of one drop of the Jones reagent had changed to green before addition of the next drop. The resulting mixture was then stirred at 15°–20° C. for 90 minutes. The reaction mixture was diluted with sufficient water to dissolve the precipitated chromium salts and was then extracted four times with diethyl ether. The combined ether extracts were washed with water, and then extracted three times with aqueous 2N sodium carbonate solution. The combined aqueous solutions were then acidified to pH 1 by the dropwise addition of concentrated hydrochloric acid and extracted twice with diethyl ether. The combined ethereal extracts were dried over magnesium sulphate and evaporated in vacuo to give an oil which crystallised on standing. Recrystallisation from a mixture of petroleum ether (b.p. 40°–60° C.) and diethyl ether gave 7-(5-oxocyclopent-1-enyl)heptanoic acid (28 g), m.p. 41°–43° C.

Elemental analysis: found C, 68.1; H, 8.8%; $C_{12}H_{18}O_3$ requires C, 68.5; H, 8.6%.

The 2-(7-hydroxheptyl)cyclopent-2-enone used as a starting material in the above preparation was prepared as follows:

A mixture of 7-(2-tetrahydropyranyloxy)heptanal (22 g) and 1-morpholinocyclopentene (21.4 g), i.e. the morpholine enamine of cyclopentanone, in benzene (25 ml) was heated under reflux for 12 hours under nitrogen, and the water liberated was continuously removed with a Dean and Stark head. Benzene (10 ml) and then, dropwise, 18% hydrochloric acid (28 ml) were added and the mixture was stirred for 2 hours. The organic layer was separated and evaporated. Concentrated hydrochloric acid (72 ml) and butanol (300 ml) were added to the residue. The mixture was heated at 100° C. for 1 hour, and then the solution was concentrated to give an oil. Diethyl ether was added and the ether solution was washed with aqueous sodium bicarbonate and then water, and dried over sodium sulphate. The solvent was evaporated and the residue was distilled under reduced pressure to give 2-(7-hydroxyheptyl)cyclopent-2-enone (11.7 g), b.p. 125°–170° C./0.15 mm Hg, $n_D^{25} = 1.490$, $\lambda_{max}$ 228 m$\mu$ (ethanol).

EXAMPLE 2

Methyl (±)-7-[4-acetoxy-5-oxo-cyclopent-1-enyl]heptanoate

A solution of (±)-7-[4-acetoxy-5-oxo-cyclopent-1-enyl]heptanoic acid (1.0 g; prepared as described in Example 1) in dry diethyl ether (10 ml) was treated with a solution of diazomethane (0.32 g) in dry diethyl ether (5 ml). The reaction mixture was allowed to stand at ambient temperature for 2.5 hours. The diethyl ether and excess diazomethane were removed in vacuo to yield methyl (±)-7-[4-acetoxy-5-oxocyclopent-1-enyl]-heptanoate (1.06 g). [$\nu_{max}$ 1740 cm$^{-1}$, 1720 cm$^{-1}$, 1625 cm$^{-1}$, 1380 cm$^{-1}$, 1240 cm$^{-1}$; $\lambda_{max}$ (ethanol) 232 m$\mu$; N.M.R. (approximately 10% solution in deuterochloroform); multiplets at 7.28$\delta$, 3.35–2.7$\delta$, 2.7–2.2$\delta$, 2.5–2.0$\delta$, 2.0–1.05$\delta$, doublet of doublets at 5.15$\delta$ (J=3 cycles/second and 7 cycles/second), singlets at 3.7$\delta$ and 2.1$\delta$.].

EXAMPLE 3

Methyl (±)-7-[4-acetoxy-5-xocyclopent-1-enyl]heptanoate (7.66 g; prepared as described in Example 2) was treated with a mixture of sodium carbonate (200 mg) and water (1 ml) in methanol (100 ml) and the mixture was left to stand at ambient temperature for 20 hours. The methanol was then evaporated in vacuo, the temperature being maintained at approximately 20° C.

Water (30 ml) was added to the residue and the mixture was extracted three times with diethyl ether. The combined ethereal extracts were washed with saturated aqueous sodium chloride solution, dried over magnesium sulphate, and evaporated in vacuo to give an oil, which solidified on standing. The solid was recrystallised from a mixture of petroleum ether (b.p. 40°–60° C.) and diethyl ether to give methyl (±)-7-[4-hydroxy-5-oxocyclopent-1-enyl]heptanoate (2.21 g), m.p. 62.5°–63.5° C. [Elemental analysis: found C, 65.0; H, 8.5%; $C_{13}H_{20}O_4$ requires: C, 65.0; H, 8.4%].

REFERENCE EXAMPLE

A solution of tert-butyl lithium in pentane (13.0 ml; 1.0M) was added, rapidly, using a syringe, to a stirred solution of (±)-3-(1-ethoxy)ethoxy-1-iodo-trans-oct-1-ene (2.10 g) in dry diethyl ether (50 ml) at −70° C. to −80° C. in an atmosphere of dry argon. The resultant mixture was stirred at −70° C. to −80° C. for a further period of two hours to give solution A.

Meanwhile, freshly distilled tri-n-butylphosphine (1.4 ml) was added, using a syringe, to a solution of tri-n-butylphosphine-copper (I) iodide complex (2.22 g) in dry diethyl ether in an atmosphere of dry nitrogen at ambient temperature to give solution B.

Solution B was transferred, using a syringe, to solution A and the yellow mixture obtained was stirred at −70° C. to −80° C. for 50 minutes and was then treated, dropwise, with a solution of methyl (±)-7-[4-(2-tetrahydropyranyloxy)-5-oxocyclopent-1-enyl]heptanoate (1.71 g) in dry diethyl ether (60 ml), using a syringe, maintaining the temperature between −70° C. and −80° C. The resulting mixture was stirred at between −70° C. and −80° C. for one hour, and was then warmed to between −18° C. and −23° C. and was stirred at between −18° C. and −23° C. for 45 minutes. The mixture was then treated, dropwise, with an aqueous solution of ammonium sulphate (50 ml; 20% w/v), using a syringe, and the resulting mixture was then poured into a mixture of diethyl ether (100 ml) and cold aqueous ammonium sulphate solution (50 ml; 20% w/v). The aqueous layer was separated and extracted three times with diethyl ether. The extracts were combined with the ethereal layer and washed with aqueous ammonium sulphate solution (20% w/v) and then with saturated aqueous sodium chloride solution, dried over magnesium sulphate, and evaporated in vacuo (maintaining the temperature below 40° C.) to give a pale brown oil (6.88 g). This brown oil (6.70 g) was treated with a mixture of glacial acetic acid (65 ml), water (35 ml) and tetrahydrofuran (10 ml), and the mixture was left to stand at 40° C. for 20 hours. The mixture was evaporated in vacuo (maintaining the temperature below 40° C.). Toluene (20 ml) was added to the residue and the mixture was evaporated again, to remove final traces of acetic acid and water, to give a pale brown oil (6.30 g) as residue.

A portion of this residue (2.40 g) was chromatographed on silica gel column (140 g), eluting with a mixture of distilled ethyl acetate and distilled cyclohexane (1:2 by volume), to produce two diastereoisomeric components of methyl 7-[2-(3-hydroxyoct-trans-1-enyl)-4-hydroxy-5-oxocyclopentyl]heptanoate.

By analogy with known prostaglandins the material (25 mg) closer to the origin (component "4a") was thought to be (±)-(10R and S, 15S)-11-deoxy-10-hydroxyprostaglandin $E_1$ methyl ester [N.M.R. (approximately 5% w/v solution in deuterochloroform): multiplets at 0.85–1.0δ, 1.05–1.95δ, 2.0–1.5δ 2.5–2.9δ, 3.8–4.4δ and 5.4–5.8δ, singlet at 3.65δ]. Component 4a (25 mg) was purified further by thin layer chromatography on silica gel, eluting with a mixture of dichloromethane and acetone (7:3 by volume) and the purified product (7.3 mg) was examined by mass spectrum (molecular ion at 368, strong ions at 297, 265 and 247).

The material (30 mg) farther from the origin in the column chromatograph (component "4b") was thought to be (±)-(10R and S, 15R)-11-deoxy-10-hydroxyprostaglandin $E_1$ methyl ester. The N.M.R. spectrum of component 4b was identical with that of component 4a. Component 4b (30 mg) was purified further by thin layer chromatography under conditions similar to those used for component 4a and the purified product (10.5 mg) had a mass spectrum identical with that of purified component 4a.

The methyl (±)-7-[4-(2-tetrahydropyranyloxy)-5-oxocyclopent-1-enyl]heptanoate, used as a starting material, was prepared as follows:

A solution of p-toluenesulphonic acid (20 mg) in dry dichloromethane (5 ml) was added, dropwise, to a stirred mixture of methyl (±)-7-[4-hydroxy-5-oxocyclopent-1-enyl]-hepatanoate (1.2 g; prepared as described in Example 3) and 2,3-dihydropyran in dry dichloromethane (20 ml), with cooling to maintain the temperature below 30° C. After one hour, a further quantity of 2,3-dihydropyran (0.3 g) was added dropwise, and the mixture was stirred for one hour further. Pyridine (100 mg) was added, and the mixture was washed with saturated aqueous sodium chloride solution, dried over magnesium sulphate, and evaporated in vacuo, finally at 0.1 mm Hg and 50° C. for 4 hours, to give methyl (±)-7-[4-(2-tetrahydropyranyloxy)-5-oxocyclopent-1-enyl]heptanoate (1.9 g), in the form of a brown oil, pure enough for use in the next stage without further purification.

The present invention includes within its scope pharmaceutical compositions which comprise at least one cyclopentane derivative of formula I or, when $R^2$ represents a hydrogen atom, a non-toxic salt thereof, together with a pharmaceutical carrier or coating. In clinical practice the novel compounds of the present invention will normally be administered orally, rectally, vaginally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time.

In general, the preparations should normally contain at least 0.025% by weight of active substance when required for administration by injection; for oral administration the preparations will normally contain at least 0.1% by weight of active substances. The dose employed depends upon the desired therapeutic effect, the route of administration and the duration of the treatment. In the adult, the doses are generally between 0.0002 and 2.0 mg/kg body weight by intravenous administration, preferably by intravenous infusion at a rate of between 0.0001 and 1.0 mg/kg body weight/minute, as hypertensives, and between 0.001 and 0.3 mg/kg body weight orally as inhibitors of gastric acid secretion. If necessary these doses may be repeated as and when required.

The following Example illustrates pharmaceutical compositions according to the invention.

EXAMPLE 4

(±)-7-(4-Acetoxy-5-oxocyclopent-1-enyl)heptanoic acid (300 mg) was dissolved in ethanol (1 ml) and the solution obtained was added to an aqueous solution (12 ml) containing sodium carbonate (50 mg). Aqueous sodium chloride solution (0.9% w/v; 2 ml) was then added to give a final volume of 15 ml. The solution was then sterilized by passage through a bacteria-retaining filter and placed in 1.5 ml portions in 5 ml ampoules, to give 30 mg of the heptanoic acid derivative (in the form of its sodium salt) per ampoule. The contents of the ampoules were freeze-dried and the ampoules sealed. The contents of an ampoule in a suitable volume, e.g. 2 ml, of sterile water or physiological saline gave a solution ready for administration by injection.

We claim:

1. A cyclopentane derivative of the formula:

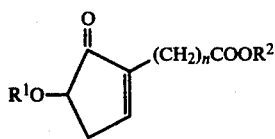

wherein $R^1$ represents hydrogen, alkanoyl of 1 to 5 carbon atoms, or benzoyl, $R^2$ represents hydrogen or alkyl of 1 through 12 carbon atoms, and n represents an integer from 4 through 8 and, when $R^2$ represents a hydrogen atom, non-toxic pharmaceutically acceptable salts thereof.

2. Cyclopentane derivatives according to claim 1 wherein $R^2$ represents hydrogen or alkyl of 1 through 4 or 7 through 12 carbon atoms.

3. Cyclopentane derivatives according to claim 1 wherein n represents 6.

4. Cyclopentane derivatives according to claim 1 wherein $R^2$ represents hydrogen or alkyl of 1 through 4 or 7 through 12 carbon atoms, and n represents 6.

5. The cyclopentane derivative according to claim 1 which is (±)-7-(4-acetoxy-5-oxocyclopent-1-enyl)heptanoic acid, and non-toxic pharmaceutically acceptable salts thereof.

6. The cyclopentane derivative according to claim 1 which is methyl (±)-7-[4-acetoxy-5-oxocyclopent-1-enyl]heptanoate.

7. The cyclopentane derivative according to claim 1 which is methyl (±)-7-[4-hydroxy-5-oxocyclopent-1-enyl]heptanoate.

8. A pharmaceutical composition for use in the treatment of prevention of low blood pressure by producing a rise in blood pressure or in the inhibition of gastric acid secretion which comprises, as active ingredient, an effective amount of a cyclopentane derivative of the formula specified in claim 1 or, when $R^2$ in that formula represents a hydrogen atom, a non-toxic pharmaceutically acceptable salt thereof together with a pharmaceutical carrier.

* * * * *